United States Patent [19]

Chen et al.

[11] Patent Number: 5,107,056
[45] Date of Patent: Apr. 21, 1992

[54] SELECTIVE SEPARATION OF NAPHTHENES FROM PARAFFINS BY MEMBRANE EXTRACTION

[75] Inventors: Tan-Jen Chen, Clearwater, Canada; James R. Sweet, Baton Rouge, La.

[73] Assignee: Exxon Research and Engineering Company, Florham Park, N.J.

[21] Appl. No.: 622,442

[22] Filed: Dec. 5, 1990

[51] Int. Cl.$^5$ .................. C07C 7/144; B01D 11/00
[52] U.S. Cl. ............................. 585/818; 208/308; 210/644; 210/650; 210/651
[58] Field of Search ............ 585/818, 819; 210/644, 210/650, 651; 208/308

[56] References Cited

U.S. PATENT DOCUMENTS

| | | | |
|---|---|---|---|
| 2,947,687 | 8/1960 | Lee | 210/23 |
| 2,956,112 | 5/1961 | Lee et al. | 210/22 |
| 3,043,891 | 7/1962 | Stuckey | 260/674 |
| 3,140,256 | 7/1964 | Martin et al. | 210/23 |
| 3,244,763 | 4/1966 | Cahn | 260/677 |
| 4,532,347 | 7/1990 | Vaughan | 562/528 |
| 4,670,151 | 6/1987 | Bitter et al. | 210/641 |
| 4,966,707 | 10/1990 | Cussler et al. | 210/632 |

OTHER PUBLICATIONS

"The Sheel Hybrid Process, An Optimized Route for HVI (High Viscosity Index) Luboil Manufacture", Bijwaard et al., Paper for the Petroleum Refining Conference of the Japan Petroleum Institute, Oct. 27–28, 1986, pp. 307–314.
"Microporous Membrane Solvent Extraction", Prasad, R. et al., Separation Science & Technology 22 (2&3), 619–640 (1987).
"Dispersion–Free Solvent Extraction with Microporous Holl Fiber Modules", Prasad, R. et al., AIChE Summer National Meeting, Boston 1986.
"Designing Hollow–Fiber Contactors", Yang, M. C. et al., AIChE Journal, Nov. 1986, vol. 32, No. 11, pp. 1910–1916.
"Liquid–Liquid Extractions with Microporous Hollow Fibers", D'Elia, N.A. et al., J. Memb. Sci. 29 (1986), 309–319.
"Critical Entry Pressure for Liquids in Hydrophobic Membranes", Kim, B. S. et al., J. Coll & Interface Science, vol. 115, No. 1, 1987, pp. 1–8.
"Solvent Extraction with Microporous Hydrophilic and Composite Membranes", Prasad, R. et al., AIChE Journal, vol. 33, No. 7 (1987), pp. 1057–1066.
"Dispersion–Free Solvent Extraction with Microporous Hollow Fiber Modules", Prasad, R. et al., AIChE Journal, vol. 34, No. 2 (1988), pp. 177–187.
"Nondispersive Solvent Extraction Using Microporous Membranes", Prasad, R. et al., AIChE Symposium Series, Membrane Materials & Processes, No. 261, vol. 84, 1988, pp. 42–53.
"Hollow Fiber Solvent Extraction of Pharmaceutical Products: A Case Study", Prasad, R. et al., J. Memb. Sci. 47 (1989), 235–259.
"Novel Uses of Microporous Membranes: A Case Study", R. W. Callahan, AIChE Symposium Series, Membrane Materials & Processes, No. 261, vol. 84, 1988, pp. 54–65.

Primary Examiner—Anthony McFarlane
Assistant Examiner—Nhat Phan
Attorney, Agent, or Firm—Joseph J. Allocca

[57] ABSTRACT

Naphthenic hydrocarbons are separated from aliphatic rich hydrocarbon feeds comprising mixtures of naphthenes with paraffinic hydrocarbons by a membrane extraction process whereby the hydrocarbon feed is contacted with one face of a porous, non-selective partition barrier membrane while simultaneously contacting the other side of said membrane with a polar solvent such as ethylenediamine. The naphthenic hydrocarbon preferentially migrates through the porous membrane partition barrier in response to the polar solvent present on the permeate side of the barrier.

5 Claims, No Drawings

SELECTIVE SEPARATION OF NAPHTHENES FROM PARAFFINS BY MEMBRANE EXTRACTION

BACKGROUND OF THE INVENTION

The present invention is a process whereby aliphatic hydrocarbon rich feed streams containing a mixture of naphthenic hydrocarbons and paraffinic hydrocarbons can be selectively separated into paraffinic rich streams and naphthenic rich streams by a process involving contacting the aliphatic hydrocarbon rich feed stream with one side of a nonselective, porous, partition barrier membrane while simultaneously contacting the other side of the partition barrier membrane with a polar solvent such as ethylene diamine. The naphthenic hydrocarbons selectively and preferentially permeate through the porous, non-selective hydrophobic partition barrier membrane in response to the polar solvent present on the permeate side of said membrane.

The porous partition barrier membrane, although not contributing to the selectivity of the separation process, does prevent or minimize the intermingling of the feed and the selective, polar extraction solvent, intermingling typical of conventional solvent extraction processes. The membrane permits the feed and the polar extraction solvent to share a large contacting surface area while preventing the intermingling of the two streams. The naphthenes selectively permeate through the barrier in response to the polar extraction solvent to produce a naphthenes rich permeate stream.

DESCRIPTION OF THE RELATED ART

Although it is not commonly practiced because of the difficulty involved in separating molecules of the same or similar boiling point, it is desirable to reduce the naphthenics level of various hydrocarbon streams such as high cetane/jet/diesel streams and lube raffinates.

In petroleum refining the hydrocarbon distillate is typically subjected to selective solvent extraction to remove undesirable aromatic hydrocarbons as an extract phase and to produce an aliphatic rich raffinate which is then dewaxed and used as a lubricating oil base stock or otherwise disposed.

In lubricant manufacture the raffinate stream contains both naphthenes and paraffinic hydrocarbons. Removal of the naphthenes would enhance the quality of the raffinate.

Because the naphthenes and the paraffins in the raffinate possess the same or essentially similar boiling ranges, separation by distillation is not possible.

Similarly, liquid-liquid extraction to remove naphthenes using solvents which are selective for naphthenes has not proved entirely satisfactory.

"The Shell Hybrid Process, An Optimized Route For HVI (High Viscosity Index) Luboil Manufacture" Bijwaard, et al, Paper For the Petroleum Refining Conference of the Japan Petroleum Institute, Oct. 27-28, 1986 pgs 307-314.

The Shell hybrid process produces high VI lube oil by employing one of the following process routes, solvent extraction, one stage hydroprocessing or a combination of solvent extraction and hydroprocessing depending on the particular feedstock. The use of two different processing steps permits the utilization of a wider range of feed stocks.

The reference indicates that several classes of compounds found in luboil hydrocarbon feedstocks are detrimental to base oil quality. These detrimental components include wax, nitrogen compounds, and higher aromatics. Even the saturates components can contain undesirable constituents. These undesirable saturates constituents include naphthene mono aromatics and polycyclic naphthenes which have low VI. The naphthene-mono aromatics are also suspected sludge formers.

Naphthenes containing strongly branched side chains and strongly branched paraffins exhibit a low VI.

It is reported in the paper that solvent extraction has only limited feedstock flexibility because the manufacture of high VI oils from feedstocks containing deficient compounds of a mainly naphthenic character is not feasible, irrespective of the solvent-to-oil ratio applied in the extraction step.

Other techniques have been put forward to separate naphthenes from paraffins.

The use of selective membranes has been suggested. U.S. Pat. No. 2,947,687 and U.S. Pat. No. 3,043,891 disclose the separation of hydrocarbon mixtures by passing across the face of a non-porous membrane through which at least one component of the hydrocarbon mixture will permeate.

U.S. Pat. No. 3,043,891 teaches a process for increasing the permeation rate of saturated hydrocarbons through non-porous membranes which are capable of separating hydrocarbons according to type, and/or molecular configuration, and/or boiling point or molecular weight. The patent teaches that the permeation process is increased by contacting the membrane during the permeation process with an added hydrocarbon solvent for the membrane. This solvent may contact the membrane on the feed side, the permeate side or on both sides. Representative of such permeation accelerating solvents include aromatics and unsaturated hydrocarbons such as olefins or diolefins. The solvent is described as being a solvent for the membrane, i.e., swells the membrane.

The membranes employed are described as non-porous and include natural or synthetic rubber, gum rubber, chloroprene, neoprene, vinyl polymers such as styrene polymer, polyisobutylene, certain cellulose ethers.

The patent indicates that saturated molecules will permeate through the membrane in the following sequence of increasing selectivity: open chain highly branched hydrocarbons, <open chain with lesser degree of branching; <closed chain (e.g. cycloparaffins) and alkyl cycloparaffins, <straight chain or normal paraffins. Use of the membrane solvent will substantially increase the permeation without substantially altering the selectivity.

U.S. Pat. No. 2,947,687 teaches the separation of hydrocarbons by type through a non-porous membrane using a membrane solvent to enhance the permeation rate. Membrane solvents include substituted hydrocarbons which are soluble in and have solvent power for the membrane. The hydrocarbon solvent is an organic compound containing one or more atoms of halogen, oxygen, sulfur or nitrogen. Thus, materials such as carbontetrachloride, alcohols, ketones, esters, ethers, carboxylic acids, mercaptans, sulfides (e.g. diethylsulfide etc.), nitropropane, nitrobenzene, acetonitrile, formamide, ethylene diamine. etc. may be employed in an amount ranging from 1 to 100% based on total solvent to hydrocarbon feed. The process may be operated at a pressure differential between the feed and permeate zone with the permeate being removed by vacuum. Alternately the permeate can be removed by a sweep stream such as steam, air, butane, etc.

The membrane is non-porous and includes natural or synthetic rubber, vinyl polymers, cellulose esters, cellulose ethers.

The process can use any hydrocarbon source as feed and the separation achieved is in the order: saturated hydrocarbons, <unsaturated hydrocarbons, <aromatics. Saturated hydrocarbons of approximately the same boiling range permeate in the order of increasing selectivity: branched chain, <cyclic-chain, <straight chain configuration, i.e., straight chain paraffins more readily permeate through the membrane.

In an example methyl cyclohexane is separated from an equal volume mixture of methyl cyclohexane and isooctane using 5% methyl ethyl ketone as solvent. An operating pressure differential of 400 mm Hg was maintained and the temperature was 52° C. and 82° C. The methyl cyclohexane preferentially permeated through the membrane.

U.S. Pat. No. 3,956,112 teaches a membrane solvent extraction process. The membrane solvent extraction system is utilized to separate two substantially immiscible liquids and extract a solute through a solvent swollen membrane from one solvent liquid phase to the extracting solvent liquid without direct contact between the liquid phases. The membrane is substantially non-porous. Table III of U.S. Pat. No. 3,956,112 compares the invention of '112 with competing processes. One of these processes is described as direct extraction via porous partition. That process is practiced using two immiscible solvents. The driving force is the chemical potential depending on the partition coefficient of the solute in the two solvents. The process employs a porous membrane or partition wall. In that process solutes from one solvent are transferred to the extraction solvent via direct solventsolvent contact.

U.S. Pat. No. 3,140,256 teaches a membrane separation process employing a membrane comprised of a cellulose derivative (eg cellulose ester or ether) modified by reaction with aldehydes, organic di isocyanate, organic monoisocyanate, organo-phosphorus chlorides and organo-sulfur chlorides. Hydrocarbon feeds can be separated into these components by type using the membrane, eg aromatics can be separated from unsaturated hydrocarbon (olefins or di olefins) and/or from paraffins, or branched chain aliphatic hydrocarbons can be separated from other aliphatic hydrocarbons which have a different number of branched chains. Aromatic hydrocarbons permeate more rapidly than do the saturated (i.e. paraffinic) hydrocarbons. In an example methyl cyclohexane permeated through the membrane more selectively than did iso octane.

"Microporous Membrane Solvent Extraction" Prasad, R., et al, Separation Science and Technology 22(2&3) 619–640, 1987 examines the phenomenon of dispersion-free solvent extraction through immobilized aqueous-organic interface in a microporous hydrophobic membrane. Expressly investigated was the use of an organic-organic interface to extract aromatics as exemplified by toluene, from a hydrocarbon feedstock, as exemplified by a mixture of toluene in n-heptane, employing a microporous Celgard 2400 polypropylene membrane to partition the feed from the polar extraction solvent, which in this case was NMP. The toluene selectively permeated through the porous Celgard membrane into the NMP thereby reducing the amount of toluene in the feed (raffinate) while increasing the amount of toluene in the permeate phase (extract).

SUMMARY OF THE INVENTION

Hydrocarbon feed mixtures of naphthenic and paraffinic hydrocarbons are separated by passing the feed mixture across one face of a non-selective microporous partition barrier membrane while simultaneously passing a polar solvent along the other face of said membrane whereby the naphthenic hydrocarbons selectively permeate through the membrane in response to the polar solvent on the other side of the membrane resulting in a naphthenes rich permeate.

DESCRIPTION OF THE PREFERRED EMBODIMENTS

Aliphatic hydrocarbon mixtures substantially comprising mixtures of naphthenic hydrocarbons and paraffinic hydrocarbons are separated into a naphthenes rich stream and a paraffins rich stream by a process wherein the mixture is contacted with one side of a porous, non-selective, partition barrier membrane and the naphthenic hydrocarbons selectively pass through the porous, non-selective, partition barrier membrane in response to a polar solvent passing preferably countercurrently along the opposite face of the partition barrier membrane.

The feed to the membrane separation process of the present invention is described as an aliphatic rich hydrocarbon stream substantially comprising a mixture of naphthenes and paraffins. This stream can be obtained either naturally, such as by the production of a naphthenic crude oil source or, more usually by starting with any typical hydrocarbon crude oil source, atmospheric distilling said oil to recover various atmospheric fractions, vacuum distilling the heavy atmospheric bottoms to recover various vacuum fractions, and solvent dearomatizing the oil distillate fractions boiling in the 320 to 1100° F. range. Subjecting this oil to selective aromatic solvent extraction produces an aromatics rich extract phase and a saturates rich raffinate phase. It is this raffinate phase which can be used as the feed to the present process.

The feed stream is passed along one side of a porous, non-selective partition barrier membrane. The barrier membrane can be described as being an ultrafiltration membrane and may be made of ceramic, sintered glass or metal, or of a polymeric material such as polyethylene, polypropylene, teflon, cellulose, nylon, etc. and generally has a pore size in the range 100 to 5000Å. The membrane is, preferably, hydrophobic in nature.

The naphthenic hydrocarbons selectively pass through this porous partition barrier in response to a polar solvent passing, preferably countercurrently, along the opposite face of the barrier membrane. Examples of such polar solvents include aliphatic polyamines such as ethylene diamine, diethylene triamine, triethylene tetramine, phenol, furfural, acetonitrile, sulfolane, dimethylsulfoxide (DMSO) and n-methyl pyrrolidone (NMP), etc. and mixtures thereof.

In the present process, the feed and extraction solvent can be contacted at any temperature so long as both the feed and solvent are in the liquid state. Because the separation process is driven by the affinity of the polar solvent for the naphthenic molecules, the process can be run at atmospheric pressure. Indeed, because of the high porosity of the membrane partition barrier the existence of a pressure differential, either by the direct application of pressure on the feed or solvent side or the creation of a vacuum on either side is undesirable as such a pressure differential would physically force feed or solvent across the barrier and thus defeat its purpose.

EXAMPLE

To illustrate the effectiveness of membranes in naphthenes/paraffins separation, a 100 neutral raffinate sample was procured. Celgard 2500 which is a polypropylene membrane with 0.04×0.20 micrometer pores was then used to partition while maintaining intimate contact between the feed and ethylenediamine which is a very polar solvent. Since ethylenediamine is very polar, naphthenes are preferentially permeated to the solvent side.

TABLE
NAPHTHENE/PARAFFIN SEPARATION BY MEMBRANE

| Stream | Feed (100N Raffinate) | Permeate |
|---|---|---|
| Membrane Extraction | | |
| Membrane | | Celgard 2500 |
| Solvent | | Ethylenediamine |
| Temperature, °C. | | 90 |
| Flux, kg/m$^2$/day | | 28 |
| Composition, LV % | | |
| Paraffins | 31.7 | 24.0 |
| Naphthenes | 50.7 | 57.4 |
| Aromatics | 17.6 | 18.6 |

As can be seen from the table, the mass spec. completed on the permeate and the raffinate feed show that naphthenes/paraffins separation was effected by the present process. The raffinate feed has 31 LV% paraffins whereas the permeate has 24 LV% paraffins.

Although the data on only a 100N raffinate are shown, it is expected that the membrane separation described in this specification to be applicable to other grades of raffinate and any other refinery stream where naphthene/paraffin separation is needed. It is also expected that other polar solvents such as sulfolane and DMSO would be effective in naphthenes/ paraffins separation. It is also expected that the separation can be extended to other micro-porous membranes such as teflon or nylon.

What is claimed is:

1. A method for separating naphthenes from aliphatic hydrocarbon-rich feed streams containing mixtures of naphthenes with paraffins comprising the steps of contacting the aliphatic hydrocarbon-rich feed stream with one side of a nonselective, porous partition barrier membrane while simultaneously contacting the other side of the partition barrier membrane with a polar solvent, in the absence of a pressure differential across the membrane, to thereby selectively permeate the naphthenic hydrocarbon through the porous partition barrier in response to the polar solvent present on the permeate side of said membrane.

2. The method of claim 1 wherein the aliphatic hydrocarbon-rich feed is a naturally occurring naphthenics-rich crude oil or is the raffinate phase recovered from paraffinic crude oil by the steps of atmospheric distillation, vacuum distillation of the heavy bottom fraction recovered from the atmospheric distillate, solvent dearomatizing the vacuum distillate fraction boiling in the 320 to 1100° F. range to produce a saturates rich raffinate.

3. The method of claim 1 wherein the porous partition barrier has a pore size in the range 100 to 5000Å.

4. The method of claim 3 wherein the porous partition barrier is selected from polyethylene, polypropylene, teflon, cellulose.

5. The method of claim 1 wherein the polar solvent is selected from aliphatic polyamines, phenol, furfurol, sulfolane, n-methylpyrrolidone, and mixtures thereof.

* * * * *